United States Patent [19]

Brenner

[11] Patent Number: 5,763,175
[45] Date of Patent: Jun. 9, 1998

[54] SIMULTANEOUS SEQUENCING OF TAGGED POLYNUCLEOTIDES

[75] Inventor: Sydney Brenner, Cambridge, England

[73] Assignee: Lynx Therapeutics, Inc., Hayward, Calif.

[21] Appl. No.: 560,313

[22] Filed: Nov. 17, 1995

[51] Int. Cl.$^6$ .............................. C12Q 1/68; C12P 19/34; C12N 15/00
[52] U.S. Cl. .............................. 435/6; 435/91.2; 935/77; 935/78
[58] Field of Search .............................. 435/6; 536/23.1, 536/24.2, 24.3; 935/76–78

[56] References Cited

U.S. PATENT DOCUMENTS

| | | | |
|---|---|---|---|
| 4,293,652 | 10/1981 | Cohen | 435/172 |
| 4,942,124 | 7/1990 | Church | 435/6 |
| 4,994,370 | 2/1991 | Silver et al. | 435/6 |
| 5,102,785 | 4/1992 | Livak et al. | 435/6 |
| 5,149,625 | 9/1992 | Church | 435/6 |
| 5,310,893 | 5/1994 | Erlich et al. | 536/24.31 |
| 5,405,746 | 4/1995 | Uhlen | 435/6 |
| 5,407,799 | 4/1995 | Studier | 435/6 |
| 5,413,909 | 5/1995 | Bassam et al. | 435/6 |
| 5,427,911 | 6/1995 | Ruano | 435/6 |
| 5,496,699 | 3/1996 | Sorenson | 435/6 |
| 5,508,169 | 4/1996 | Deugau et al. | 435/6 |

FOREIGN PATENT DOCUMENTS

| | | |
|---|---|---|
| 303 459 | 2/1989 | European Pat. Off. . |
| 90107066.4 | 10/1990 | European Pat. Off. . |
| 649 852 | 4/1994 | European Pat. Off. . |
| 630 972 | 12/1994 | European Pat. Off. . |
| PCT/US92/01905 | 9/1992 | WIPO . |
| PCT/US93/01552 | 9/1993 | WIPO . |
| PCT/GB93/01452 | 1/1994 | WIPO . |
| PCT/US94/07086 | 1/1995 | WIPO . |
| PCT/GB94/01675 | 2/1995 | WIPO . |
| PCT/GB95/00109 | 7/1995 | WIPO . |
| PCT/US95/03678 | 10/1995 | WIPO . |

OTHER PUBLICATIONS

Gramegna et al., Research in Virology 144:307–309 (1993).
Szybalski, Gene 135: 279–290 (1993).
Martin, Genome 31: 107–1080 (1989).
McBride et al., Clinical Chemistry 35(11):2196–2201 (1989).
Berg et al. Biotechniques 17(5):896–901 (1994).
Kasai et al., Nucleic Acids Research20(24): 6509–6515 (1992).
Boles et al., Current Genetics 28: 197–198 (1995).
Wu et al., PNAS 86:2757–2760 (1990).
Scharf et al., PNAS 86:6215–6219 (1990).

Okayama et al., J. Laboratory and Clinical Medicine 114(2): 105–113 (1989).
Roberts and Macelis, "Rebase–restriction enzymes and methylases," Nucleic Acids Research, 21: 3125–3137 (1993).
Hasan et al., "A novel multistep method for generating precise unidirectional deletions using BspMi, a class–IIS restriction enzyme," Gene, 50: 55–62 (1986).
Hasan et al., "An MboII/FokI trimming plasmid allowing consecutive cycles of precise 1–to 12–base–pair deletions in cloned DNA," Gene, 82: 305–311 (1989).
Syzbalski et al., "Class–IIS restriction enzymes—a review," Gene, 100:013–26 (1991).
Kwok et al., "Effects of primer–template mismatches on the polymerase chain reaction: Human immunodeficiency virus type 1 model studeis," Nucleic Acids Research, 18: 999–1005 (1990).
Huang et al., "Extension of base mispairs by Taq DNA polymerase: implications for single nucleotide discrimination in PCR," Nucleic Acids Research 20: 4567–4573(1992).
Short Technical Reports, "Priming Efficiency," BioTechniques, 18: 84–89 (1995).
Martin and Castro, "Base pairing involving deoxyinosine: implications for probe design," Nucleic Acids Research, 13: 8927–8938 (1985).
Kawase et al., "Studies on nucleic acid interactions 1. Stabilities of mini–duplexes ($dG_2A_4XA_4G_2 \cdot dC_2T_4YT_4C_2$) and self–complementary d(GGGAAXYTTCCC) containing deoxyinosine and other mismatched bases," Nucleic Acids Research, 14: 7727–7736 (1986).
Case–Green and Southern, "Studies on the base pairing properties of deoxyinosine by solid phase hybridisation to oligonucleotides," Nucleic Acids Research, 22: 131–139 (1994).
Ausubel et al., "Mutagenesis of Cloned DNA," Current Protocols in Molecular Biology, Chapter 8, John Wiley & Sons, 1995.
Mormeneo et al, "Precise nucleotide sequence modifications with bidirectionally cleaving class–IIS excision linkers," Gene, 61: 21–30 (1987).

(List continued on next page.)

Primary Examiner—W. Gary Jones
Assistant Examiner—Ethan Whisenant
Attorney, Agent, or Firm—Stephen C. Macevicz

[57] ABSTRACT

The invention provides a method for sequencing each polynucleotide of a population by using an oligonucleotide tag assigned to each such polynucleotide for transfering sequence information to a tag complement located on a spatially addressable array of such complements. That is, a unique tag is attached to each polynucleotide of a population which can be copied and used to shuttle sequence information to its complement at a fixed position on an array of such complements. After a tag hybridizes with its complement, a signal is generated that is indicative of the transferred sequence information. Sequences of the tagged polynucleotides are determined by repeated cycles of information transfer and signal detection at the positions of the corresponding tag complements.

13 Claims, 3 Drawing Sheets

OTHER PUBLICATIONS

Unrau and Deugau, "Non-cloning amplification of specific DNA fragments from whole genomic DNA digests using DNA 'indexers '," Gene, 145: 163–169 (1994).

Kato, "Description of the entire mRNA population by a 3'end cDNA fragment generated by a 3'end cDNA fragment generated by class IIS restriction enzymes." Nucleic Acids Research, 23: 3685–3690 (1995).

SIMULTANEOUS SEQUENCING OF TAGGED POLYNUCLEOTIDES

FIELD OF THE INVENTION

The invention relates generally to methods for sequencing polynucleotides, and more particularly, to a method of sorting and sequencing many polynucleotides simultaneously.

BACKGROUND

The desire to decode the human genome and to understand the genetic basis of disease and a host of other physiological states associated differential gene expression has been a key driving force in the development of improved methods for analyzing and sequencing DNA, Adams et al. Editors, Automated DNA Sequencing and Analysis (Academic Press, New York, 1994). Current genome sequencing projects use Sanger-based sequencing technologies, which enable the sequencing and assembly of a genome of 1.8 million bases with about 24 man-months of effort, e.g. Fleischmann et al, Science, 269: 496–512 (1995). Such a genome is about 0.005 the size of the human genome, which is estimated to contain about $10^5$ genes, 15% of which—or about 3 megabases—are active in any given tissue. The large numbers of expressed genes make it difficult to track changes in expression patterns by sequence analysis. More commonly, expression patterns are initially analyzed by lower resolution techniques, such as differential display, indexing, substraction hybridization, or one of the numerous DNA fingerprinting techniques, e.g. Liang et al, Science, 257: 967–971 (1992); Erlander et al, International patent application PCT/US94/13041; McClelland et al, U.S. Pat. No. 5,437,975; Unrau et al, Gene, 145: 163–169 (1994); and the like. Sequence analysis is then frequently carried out on subsets of cDNA clones identified by application of such techniques, e.g. Linskens et al, Nucleic Acids Research, 23: 3244–3251 (1995). Such subsequent analysis is invariably carried out using conventional Sanger sequencing of randomly selected clones from a subset; thus, the scale of the analysis is limited by the Sanger sequencing technique.

Recently, two techniques have been reported that attempt to provide direct sequence information for analyzing patterns of gene expression, Schena et al, Science, 270: 467–469 (1995) (hybridizing mRNA to 45 expressed sequence tags attached to a glass slide) and Velculescu et al, Science, 270: 484–486 (1995) (excision and concatination of short tags adjacent to type IIs restriction sites in sequences from a cDNA library, followed by Sanger sequencing of the concatinated tags). However, implementation of these techniques has only involved relative few sequences (45 and 30, respectively) so it is not clear whether they have the capability to track a more meaningful sample of expressed genes, e.g. Kollner et al, Genomics, 23: 185–191 (1994). Without substantially larger sample sizes, the techniques will not be able to track changes in the transcript levels of low-expression genes.

It is clear from the above that there is a crucial need both for higher throughput sequencing techniques that can reduce the time and effort required to analyze genome-sized DNAs and that can be applied to the analysis of large samples of sequences from complex mixtures of polynucleotides, such as cDNA libraries. The availability of such techniques would find immediate application in medical and scientific research, drug discovery, diagnosis, forensic analysis, food science, genetic identification, veterinary science, and a host of other fields.

SUMMARY OF THE INVENTION

An object of my invention is to provide a new method and approach for determining the sequence of polynucleotides.

Another object of my invention is to provide a method for rapidly analyzing patterns of gene expression in normal and diseased tissues and cells.

A further object of my invention is to provide a method, kits, and apparatus for simultaneously analyzing and/or sequencing a population of many thousands of different polynucleotides, such as a sample of polynucleotides from a cDNA library or a sample of fragments from a segment of genomic DNA.

Still another object of my invention is to provide a method, kits, and apparatus for identifying populations of polynucleotides.

Another object of my invention is to provide a method for sequencing segments of DNA in a size range corresponding to typical cosmid or YAC inserts.

My invention achieves these and other objectives by providing each polynucleotide of a population with an oligonucleotide tag for transfering sequence information to a tag complement on spatially addressable array of such complements. That is, a unique tag is attached to each polynucleotide of a population which can be copied and used to shuttle sequence information to its complement at a fixed position on an array of such complements. After a tag hybridizes with its complement, a signal is generated that is indicative of the transferred sequence information. Sequences of the tagged polynucleotides are determined by repeated cycles of information transfer and signal detection at the positions of the corresponding tag complements.

At least two major advantages are gained by using tags to shuttle information to discrete spatial locations rather than sorting an entire population of target polynucleotides to such locations: First, tags are much smaller molecular entities so that the kinetics of diffusion and hybridization are much more favorable. Second, tag loading at the spatially discrete locations only need be sufficient for detection, while target polynucleotide loading would need to be sufficient for both biochemical processing and detection; thus, far less tag needs to be loaded on the spatially discrete sites.

An important aspect of my invention is the attachment of an oligonucleotide tag to each polynucleotide of a population such that substantially all different polynucleotides have different tags. As explained more fully below, this is achieved by taking a sample of a full ensemble of tag-polynucleotide conjugates wherein each tag has an equal probability of being attached to any polynucleotide. The sampling step ensures that the tag-polynucleotide conjugate population will fulfill the above-stated condition that the tag of any polynucleotide of such population be substantially unique.

Oligonucleotide tags employed in the invention are capable of hybridizing to complementary oligomeric compounds consisting of subunits having enhanced binding strength and specificity as compared to natural oligonucleotides. Such complementary oligomeric compounds are referred to herein as "tag complements." Subunits of tag complements may consist of monomers of non-natural nucleotide analogs or they may comprise oligomers having lengths in the range of 3 to 6 nucleotides or analogs thereof, the oligomers being selected from a minimally cross-hybridizing set. In such a set, a duplex made up of an oligomer of the set and the complement of any other oligomer of the set contains at least two mismatches. In other words, an oligomer of a minimally cross-hybridizing set at best forms a duplex having at least two mismatches with the complement of any other oligomer of the same set. The number of oligonucleotide tags available in a particular embodiment depends on the number of subunits per tag and on the length of the subunit, when the subunit is an oligomer from a minimally cross-hybridizing set. In the latter case, the number is generally much less than the number of all possible sequences the length of the tag, which for a tag n nucleotides long would be $4^n$. Preferred monomers for complements include peptide nucleic acid monomers and nucleoside phosphoramidates having a 3'-NHP(O)(O-)O-5' linkage with its adjacent nucleoside. The latter compounds are referred to herein as N3'→P5' phosphoramidates. Preferably, both the oligonucleotide tags and their tag complements comprise a plurality of subunits selected from a minimally cross-hybridizing set consisting of natural oligonucleotides of 3 to 6 nucleotides in length.

Generally, the method of my invention is carried out by the following steps: (a) attaching an oligonucleotide tag from a repertoire of tags to each polynucleotide of a population to form tag-polynucleotide conjugates such that substantially all different polynucleotides have different oligonucleotide tags attached; (b) labeling each tag according to the identity of one or more terminal nucleotides of its associated polynucleotide; (c) cleaving the tags from the tag-polynucleotide conjugates; and (d) sorting the labeled tags onto a spatially addressable array of tag complements for detection. Preferably, the identity of the one or more terminal nucleotides is determined by selectively amplifying correct sequence primers in a polymerase chain reaction (PCR) employing primers whose 3' terminal sequences are complementary to every possible sequence of the one or more terminal nucleotides whose identity is sought. Thus, when the identity of a single terminal nucleotide is sought, four separate polymerase chain reactions may be carried out with one primer identical in each of the four reactions, but with each of the other four primers having a 3' terminal nucleotide that is either A, C, G, or T. As used herein, this terminal nucleotide is referred to as a defined 3' terminal nucleotide. The 3' terminal nucleotide is positioned so that it must be complementary to the terminal nucleotide of the target polynucleotide for amplification to occur. Thus, the identity of the primer in a successful amplification gives the identity of the terminal nucleotide of the target sequence. This information is then extracted in parallel from the population of target polynucleotides by detaching the amplified tags and sorting them onto their tag complements on a spatially addressable array. By repeating this process for successive nucleotides the sequences of a population of target polynucleotides are determined in parallel.

My invention provides a readily automated system for obtaining sequence information from large numbers of target polynucleotides at the same time. My invention is particularly useful in operations requiring the generation of massive amounts of sequence information, such as large-scale sequencing of genomic DNA fragments, mRNA and/or cDNA fingerprinting, and highly resolved measurements of gene expression patterns.

DEFINITIONS

Figure 1:
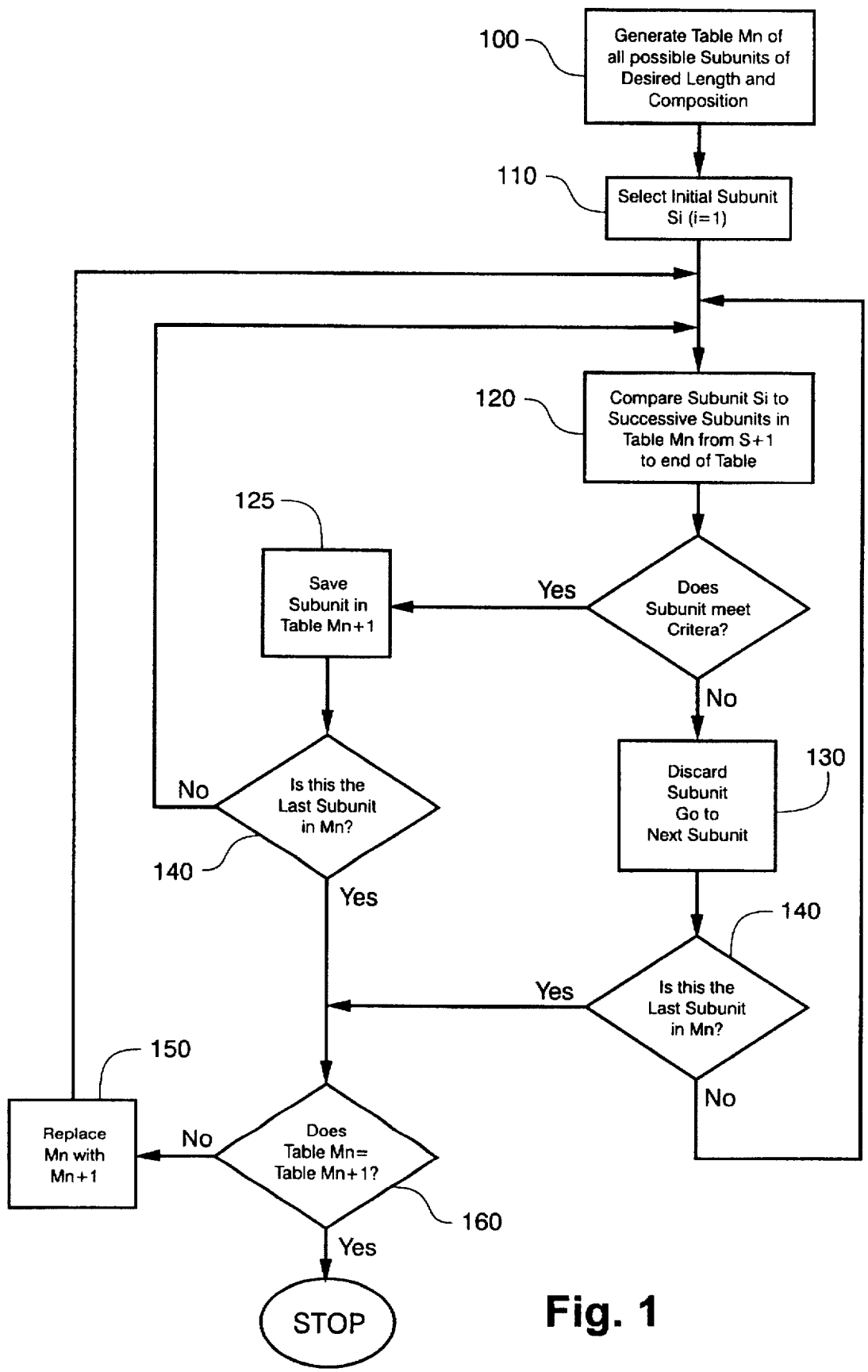
FIG. 1 is a flow chart illustrating a general algorithm for generating minimally cross-hybridizing sets.

"Complement" or "tag complement" as used herein in reference to oligonucleotide tags refers to an oligonucleotide to which a oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

The term "oligonucleotide" as used herein includes linear oligomers of natural or modified monomers or linkages, including deoxyribonucleosides, ribonucleosides, -anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3–4, to several tens of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate, phosphoramidate, and the like. It is clear to those skilled in the art when oligonucleotides having natural or non-natural nucleotides may be employed, e.g. where processing by enzymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleosides designed to enhance binding properties, reduce degeneracy, increase specificity, and the like.

DETAILED DESCRIPTION OF THE INVENTION

The invention provides a method of sequencing large numbers of polynucleotides in parallel by using oligonucleotide tags to shuttle sequence information obtained in "bulk" or solution phase biochemical processes to discrete spatially addressable sites on a solid phase. Signals generated at the spatially addressable sites convey the sequence information carried by the oligonucleotide tag. As explained more fully below, sequencing is preferably carried out by alternating cycles of identifying nucleotides and shortening the target polynucleotides. In the shortening cycles, a predetermined number of previously identified nucleotides are cleaved from the target polynucleotides and the shortened polynucleotides are employed in the next cycle of nucleotide identification.

In one aspect, the oligonucleotide tags of the invention comprise a plurality of "words" or subunits selected from minimally cross-hybridizing sets of subunits. Subunits of such sets cannot form a duplex or triplex with the complement of another subunit of the same set with less than two mismatched nucleotides. Thus, the sequences of any two oligonucleotide tags of a repertoire that form duplexes will never be "closer" than differing by two nucleotides. In particular embodiments, sequences of any two oligonucleotide tags of a repertoire can be even "further" apart, e.g. by designing a minimally cross-hybridizing set such that subunits cannot form a duplex with the complement of another subunit of the same set with less than three mismatched nucleotides, and so on. Usually, oligonucleotide tags of the invention and their complements are oligomers of the natural nucleotides so that they may be conveniently processed by enzymes, such as ligases, polymerases, nucleases, terminal transferases, and the like.

In another aspect of the invention, tag complements consist of non-natural nucleotide monomers which encompass a range of compounds typically developed for antisense therapeutics that have enhanced binding strength and enhanced specificity for polynucleotide targets. As mentioned above under the definition of "oligonucleotide," the compounds may include a variety of different modifications of the natural nucleotides, e.g. modification of base moieties, sugar moieties, and/or monomer-to-monomer linkages. Such compounds also include oligonucleotide loops, oligonucleotide "clamps," and like structures that promote enhanced binding and specificity.

Constructing Oligonucleotide Tags from Minimally Cross-Hybridizing Sets of Subunits The nucleotide sequences of the subunits for any minimally cross-hybridizing set are conveniently enumerated by simple computer programs following the general algorithm illustrated in FIG. 1, and as exemplified by program minhx whose source code is listed in Appendix I. Minhx computes all minimally cross-hybridizing sets having subunits composed of three kinds of nucleotides and having length of four.

The algorithm of FIG. 1 is implemented by first defining the characteristic of the subunits of the minimally cross-hybridizing set, i.e. length, number of base differences between members, and composition, e.g. do they consist of two, three, or four kinds of bases. A table $M_n$, n=1, is generated (100) that consists of all possible sequences of a given length and composition. An initial subunit $S_1$ is selected and compared (120) with successive subunits $S_i$ for i=n+1 to the end of the table. Whenever a successive subunit has the required number of mismatches to be a member of the minimally cross-hybridizing set, it is saved in a new table $M_{n+1}$ (125), that also contains subunits previously selected in prior passes through step 120. For example, in the first set of comparisons, $M_2$ will contain $S_1$; in the second set of comparisons, $M_3$ will contain $S_1$ and $S_2$; in the third set of comparisons, $M_4$ will contain $S_1$, $S_2$, and $S_3$; and so on. Similarly, comparisons in table $M_j$ will be between $S_j$ and all successive subunits in $M_j$. Note that each successive table $M_{n+1}$ is smaller than its predecessors as subunits are eliminated in successive passes through step 130. After every subunit of table $M_n$ has been compared (140) the old table is replaced by the new table $M_{n+1}$, and the next round of comparisons are begun. The process stops (160) when a table $M_n$ is reached that contains no successive subunits to compare to the selected subunit $S_i$, i.e. $M_n = M_{n+1}$.

As mentioned above, preferred minimally cross-hybridizing sets comprise subunits that make approximately equivalent contributions to duplex stability as every other subunit in the set. Guidance for selecting such sets is provided by published techniques for selecting optimal PCR primers and calculating duplex stabilities, e.g. Rychlik et al, Nucleic Acids Research, 17: 8543–8551 (1989) and 18: 6409–6412 (1990); Breslauer et al, Proc. Natl. Acad. Sci., 83: 3746–3750 (1986); Wetmur, Crit. Rev. Biochem. Mol. Biol., 26: 227–259 (1991); and the like. For shorter tags, e.g. about 30 nucleotides or less, the algorithm described by Rychlik and Wetmur is preferred, and for longer tags, e.g. about 30–35 nucleotides or greater, an algorithm disclosed by Suggs et al, pages 683–693 in Brown, editor, ICN-UCLA Symp. Dev. Biol., Vol. 23 (Academic Press, New York, 1981) may be conveniently employed.

A preferred embodiment of minimally cross-hybridizing sets are those whose subunits are made up of three of the four natural nucleotides. As will be discussed more fully below, the absence of one type of nucleotide in the oligonucleotide tags permits target polynucleotides to be loaded onto solid phase supports by use of the 5'→3' exonuclease activity of a DNA polymerase. The following is an exemplary minimally cross-hybridizing set of subunits each comprising four nucleotides selected from the group consisting of A, G, and T:

TABLE I

| Word: | $w_1$ | $w_2$ | $w_3$ | $w_4$ |
|---|---|---|---|---|
| Sequence: | GATT | TGAT | TAGA | TTTG |
| Word: | $w_5$ | $w_6$ | $w_7$ | $w_8$ |
| Sequence: | GTAA | AGTA | ATGT | AAAG |

In this set, each member would form a duplex having three mismatched bases with the complement of every other member.

Further exemplary minimally cross-hybridizing sets are listed below in Table I. Clearly, additional sets can be generated by substituting different groups of nucleotides, or by using subsets of known minimally cross-hybridizing sets.

TABLE II

Exemplary Minimally Cross-Hybridizing Sets of 4-mer Subunits

| Set 1 | Set 2 | Set 3 | Set 4 | Set 5 | Set 6 |
|---|---|---|---|---|---|
| CATT | ACCC | AAAC | AAAG | AACA | AACG |
| CTAA | AGGG | ACCA | ACCA | ACAC | ACAA |
| TCAT | CACG | AGGG | AGGC | AGGG | AGGC |
| ACTA | CCGA | CACG | CACC | CAAG | CAAC |
| TACA | CGAC | CCGC | CCGG | CCGC | CCGG |
| TTTC | GAGC | CGAA | CGAA | CGCA | CGCA |
| ATCT | GCAG | GAGA | GAGA | GAGA | GAGA |
| AAAC | GGCA | GCAG | GCAC | GCCG | GCCC |
|  | AAAA | GGCC | GGCG | GGAC | GGAG |

TABLE II-continued

Exemplary Minimally Cross-Hybridizing Sets of 4-mer Subunits

| Set 7 | Set 8 | Set 9 | Set 10 | Set 11 | Set 12 |
|-------|-------|-------|--------|--------|--------|
| AAGA  | AAGC  | AAGG  | ACAG   | ACCG   | ACGA   |
| ACAC  | ACAA  | ACAA  | AACA   | AAAA   | AAAC   |
| AGCG  | AGCG  | AGCC  | AGGC   | AGGC   | AGCG   |
| CAAG  | CAAG  | CAAC  | CAAC   | CACC   | CACA   |
| CCCA  | CCCC  | CCCG  | CCGA   | CCGA   | CCAG   |
| CGGC  | CGGA  | CGGA  | CGCG   | CGAG   | CGGC   |
| GACC  | GACA  | GACA  | GAGG   | GAGG   | GAGG   |
| GCGG  | GCGG  | GCGC  | GCCC   | GCAC   | GCCC   |
| GGAA  | GGAC  | GGAG  | GGAA   | GGCA   | GGAA   |

The oligonucleotide tags of the invention and their complements are conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, Tetrahedron, 48: 2223–2311 (1992); Molko et al. U.S. Pat. No. 4,980,460; Koster et al. U.S. Pat. No. 4,725,677; Caruthers et al. U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are capable of specific hybridization. As mentioned above, N3'→P5' oligonucleotide phosphoramidates are preferred materials for tag complements in some embodiments. Synthesis of such compounds is described in Chen et al. Nucleic Acids Research, 23: 2661–2668 (1995). In some embodiments, tags may comprise naturally occurring nucleotides that permit processing or manipulation by enzymes, while the corresponding tag complements may comprise non-natural nucleotide analogs, such as peptide nucleic acids, or like compounds, that promote the formation of more stable duplexes during sorting.

When microparticles are used as supports, repertoires of oligonucleotide tags and tag complements are preferably generated by subunit-wise synthesis via "split and mix" techniques, e.g. as disclosed in Shortle et al. International patent application PCT/US93/03418. Briefly, the basic unit of the synthesis is a subunit of the oligonucleotide tag. Preferably, phosphoramidite chemistry is used and 3' phosphoramidite oligonucleotides are prepared for each subunit in a minimally cross-hybridizing set, e.g. for the set first listed above, there would be eight 4-mer 3'-phosphoramidites. Synthesis proceeds as disclosed by Shortle et al or in direct analogy with the techniques employed to generate diverse oligonucleotide libraries using nucleosidic monomers, e.g. as disclosed in Telenius et al, Genomics, 13: 718–725 (1992); Welsh et al, Nucleic Acids Research, 19: 5275–5279 (1991); Grothues et al, Nucleic Acids Research, 21: 1321–1322 (1993); Hartley, European patent application 90304496.4; Lam et al, Nature, 354: 82–84 (1991); Zuckerman et al, Int. J. Pept. Protein Research, 40: 498–507 (1992); and the like. Generally, these techniques simply call for the application of mixtures of the activated monomers to the growing oligonucleotide during the coupling steps.

Double stranded forms of tags may be made by separately synthesizing the complementary strands followed by mixing under conditions that permit duplex formation. Alternatively, double stranded tags may be formed by first synthesizing a single stranded repertoire linked to a known oligonucleotide sequence that serves as a primer binding site. The second strand is then synthesized by combining the single stranded repertoire with a primer and extending with a polymerase. This latter approach is described in Oliphant et al, Gene, 44: 177–183 (1986). Such duplex tags may then be inserted into cloning vectors along with target polynucleotides for sorting and manipulation of the target polynucleotide in accordance with the invention.

In embodiments where specific hybridization occurs via triplex formation, coding of tag sequences follows the same principles as for duplex-forming tags; however, there are further constraints on the selection of subunit sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments, e.g. Roberts et al, Proc. Natl. Acad. Sci., 88: 9397–9401 (1991); Roberts et al, Science, 258: 1463–1466 (1992); Distefano et al, Proc. Natl. Acad. Sci., 90: 1179–1183 (1993); Mergny et al, Biochemistry, 30: 9791–9798 (1991); Cheng et al, J. Am. Chem. Soc., 114: 4465–4474 (1992); Beal and Dervan, Nucleic Acids Research, 20: 2773–2776 (1992); Beal and Dervan, J. Am. Chem. Soc., 114: 4976–4982 (1992); Giovannangeli et al, Proc. Natl. Acad. Sci., 89: 8631–8635 (1992); Moser and Dervan, Science, 238: 645–650 (1987); McShan et al, J. Biol. Chem., 267: 5712–5721 (1992); Yoon et al, Proc. Natl. Acad. Sci., 89: 3840–3844 (1992); Blume et al, Nucleic Acids Research, 20: 1777–1784 (1992); Thuong and Helene, Angew. Chem. Int. Ed. Engl. 32: 666–690 (1993); and the like. Conditions for annealing single-stranded or duplex tags to their single-stranded or duplex complements are well known, e.g. Ji et al, Anal. Chem. 65: 1323–1328 (1993).

When oligomeric subunits are employed, oligonucleotide tags of the invention and their complements may range in length from 12 to 60 nucleotides or basepairs; more preferably, they range in length from 18 to 40 nucleotides or basepairs; and most preferably, they range in length from 25 to 40 nucleotides or basepairs. When constructed from antisense monomers, oligonucleotide tags and their complements preferably range in length from 10 to 40 monomers; and more preferably, they range in length from 12 to 30 monomers.

TABLE III

Numbers of Subunits in Tags in Preferred Embodiments

| Monomers in Subunit | Nucleotides in Oligonucleotide Tag | | |
|---|---|---|---|
|  | (12–60) | (18–40) | (25–40) |
| 3 | 4–20 subunits | 6–13 subunits | 8–13 subunits |
| 4 | 3–15 subunits | 4–10 subunits | 6–10 subunits |
| 5 | 2–12 subunits | 3–8 subunits | 5–8 subunits |
| 6 | 2–10 subunits | 3–6 subunits | 4–6 subunits |

Most preferably, oligonucleotide tags are single stranded and specific hybridization occurs via Watson-Crick pairing with a tag complement.

After chemical synthesis libraries of tags are conveniently maintained as PCR amplicons that include primer binding regions for amplification and restriction endonuclease recognition sites to facilitate excision and attachment to polynucleotides. Preferably, the composition of the primers is selected so that the right and left primers have approximately the same melting and annealing temperatures. In some embodiments, either one or both of the primers and other flanking sequences of the tags consist of three or fewer of the four natural nucleotides in order to allow the use of a "stripping" and exchange reaction to render a construct containing a tag single stranded in a selected region. Such reactions usually employ the 3'→5' exonuclease activity of a DNA polymerase, such as T4 DNA polymerase, or like enzyme, and are described in Sambrook et al, Molecular Cloning, Second Edition (Cold Spring Harbor Laboratory, New York, 1989).

Solid Phase Supports for Tag Complements

Preferably, detection of sequence information takes place at spatially discrete locations where tags hybridize to their complements. It is important that the detection of signals from successive cycles of tag transfer be associated with the same tag complement location throughout the sequencing operation. Otherwise, the sequence of signals will not be a faithful representation of the sequence of the polynucleotide corresponding to the tag and tag complement. This requirement is met by providing a spatially addressable array of tag complement. As used herein "spatially addressable" means that the location of a particular tag complement can be recorded and tracked throughout a sequencing operation. Knowledge of the identity of a tag complement is not crucial; it is only important that its location be identifiable from cycle to cycle of tag transfers. Preferably, the regions containing tag complements are discrete, i.e. non-overlapping with regions containing different tag complements, so that signal detection is more convenient. Generally, spatially addressable arrays are constructed by attaching or synthesizing tag complements on solid phase supports.

Solid phase supports for use with the invention may have a wide variety of forms, including microparticles, beads, and membranes, slides, plates, micromachined chips, and the like. Likewise, solid phase supports of the invention may comprise a wide variety of compositions, including glass, plastic, silicon, alkanethiolate-derivatized gold, cellulose, low cross-linked and high cross-linked polystyrene, silica gel, polyamide, and the like. Preferably, either a population of discrete particles are employed such that each has a uniform coating, or population, of complementary sequences of the same tag (and no other), or a single or a few supports are employed with spacially discrete regions each containing a uniform coating, or population, of complementary sequences to the same tag (and no other). In the latter embodiment, the area of the regions may vary according to particular applications; usually, the regions range in area from several μm, e.g. 3–5, to several hundred μm, e.g. 100–500.

Tag complements may be used with the solid phase support that they are synthesized on, or they may be separately synthesized and attached to a solid phase support for use, e.g. as disclosed by Lund et al, Nucleic Acids Research, 16: 10861–10880 (1988); Albretsen et al, Anal. Biochem., 189: 40–50 (1990); Wolf et al, Nucleic Acids Research, 15: 2911–2926 (1987); or Ghosh et al, Nucleic Acids Research, 15: 5353–5372 (1987). Preferably, tag complements are synthesized on and used with the same solid phase support, which may comprise a variety of forms and include a variety of linking moieties. Such supports may comprise microparticles or arrays, or matrices, of regions where uniform populations of tag complements are synthesized. A wide variety of microparticle supports may be used with the invention, including microparticles made of controlled pore glass (CPG), highly cross-linked polystyrene, acrylic copolymers, cellulose, nylon, dextran, latex, polyacrolein, and the like, disclosed in the following exemplary references: Meth. Enzymol., Section A, pages 11–147, vol. 44 (Academic Press, New York, 1976); U.S. Pat. Nos. 4,678, 814; 4,413,070; and 4,046;720; and Pon, Chapter 19, in Agrawal, editor, Methods in Molecular Biology, Vol. 20, (Humana Press, Totowa, N.J., 1993). Microparticle supports further include commercially available nucleoside-derivatized CPG and polystyrene beads (e.g. available from Applied Biosystems, Foster City, Calif.); derivatized magnetic beads; polystyrene grafted with polyethylene glycol (e.g., TentaGel™, Rapp Polymere, Tubingen Germany); and the like. Selection of the support characteristics, such as material, porosity, size, shape, and the like, and the type of linking moiety employed depends on the conditions under which the tags are used. Exemplary linking moieties are disclosed in Pon et al, Biotechniques, 6: 768–775 (1988); Webb, U.S. Pat. No. 4,659,774; Barany et al, International patent application PCT/US91/06103; Brown et al, J. Chem. Soc. Commun., 1989: 891–893; Damha et al, Nucleic Acids Research, 18: 3813–3821 (1990); Beattie et al, Clinical Chemistry, 39: 719–722 (1993); Maskos and Southern, Nucleic Acids Research, 20: 1679–1684 (1992); and the like. As described more fully below, when tag complements are attached or synthesized on microparticles, populations of microparticles are fixed to a solid phase support to form a spatially addressable array.

As mentioned above, tag complements may also be synthesized on a single (or a few) solid phase support to form an array of regions uniformly coated with tag complements. That is, within each region in such an array the same tag complement is synthesized. Techniques for synthesizing such arrays are disclosed in McGall et al, International application PCT/US93/03767; Pease et al, Proc. Natl. Acad. Sci., 91: 5022–026 (1994); Southern and Maskos, International application PCT/GB89/01114; Maskos and Southern (cited above); Southern et al, Genomics, 13: 1008–1017 (1992); and Maskos and Southern, Nucleic Acids Research, 21: 4663–4669 (1993).

Preferably, the invention is implemented with microparticles or beads uniformly coated with complements of the same tag sequence. Microparticle supports and methods of covalently or noncovalently linking oligonucleotides to their surfaces are well known, as exemplified by the following references: Beaucage and Iyer (cited above); Gait, editor, Oligonucleotide Synthesis: A Practical Approach (IRL Press, Oxford, 1984); and the references cited above. Generally, the size and shape of a microparticle is not critical; however, microparticles in the size range of a few, e.g. 1–2, to several hundred, e.g. 200–1000 μm diameter are preferable, as they facilitate the construction and manipulation of large repertoires of oligonucleotide tags with minimal reagent and sample usage.

Preferably, commercially available controlled-pore glass (CPG) or polystyrene supports are employed as solid phase supports in the invention. Such supports come available with base-labile linkers and initial nucleosides attached, e.g. Applied Biosystems (Foster City, Calif.). Preferably, microparticles having pore size between 500 and 1000 angstroms are employed.

In other preferred applications, non-porous microparticles are employed for their optical properties, which may be advantageously used when tracking large numbers of microparticles on planar supports, such as a microscope slide. Particularly preferred non-porous microparticles are the glycidal methacrylate (GMA) beads available from Bangs Laboratories (Carmel, Ind.). Such microparticles are useful in a variety of sizes and derivatized with a variety of linkage groups for synthesizing tags or tag complements. Preferably, for massively parallel manipulations of tagged microparticles, 5 μm diameter GMA beads are employed.

Attaching Tags to Target Polynucleotides

An important aspect of the invention is tagging of polynucleotides of a population, e.g. a cDNA library, such that the same tag is not attached to different polynucleotides.

tification of gene expression patterns, substantially all means that at least eighty percent of the tags have unique polynucleotides attached. More preferably, it means that at least ninety percent of the tags have unique polynucleotides attached. Still more preferably, it means that at least ninety-five percent of the tags have unique polynucleotides attached. And, most preferably, it means that at least ninety-nine percent of the tags have unique polynucleotides attached.

In a preferred embodiment, tags, polynucleotides to be sequenced, primer binding sites, and other elements for manipulating the sequences are inserted into a cloning vector to establish a base library that may be sampled and amplified as needed. For example, such a construct could have the following form:

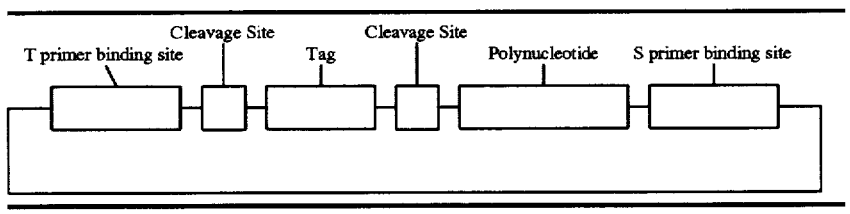

This latter condition can be essentially met by ligating a repertoire of tags to a population of polynucleotides followed by cloning and sampling of the ligated sequences. A repertoire of oligonucleotide tags can be ligated to a population of polynucleotides in a number of ways, such as through direct enzymatic ligation, amplification, e.g. via PCR, using primers containing the tag sequences, and the like. The initial ligating step produces a very large population of tag-polynucleotide conjugates such that a single tag is generally attached to many different polynucleotides. However, by taking a sufficiently small sample of the conjugates, the probability of obtaining "doubles," i.e. the same tag on two different polynucleotides, can be made negligible. (Note that it is also possible to obtain different tags with the same polynucleotide in a sample. This case is simply leads to a polynucleotide being processed, e.g. sequenced, twice). As explain more fully below, the probability of obtaining a double in a sample can be estimated by a Poisson distribution since the number of conjugates in a sample will be large, e.g. on the order of thousands or more, and the probability of selecting a particular tag will be small because the tag repertoire is large, e.g. on the order of tens of thousand or more. Generally, the larger the sample the greater the probability of obtaining a double. Thus, a design trade-off exists between selecting a large sample of tag-polynucleotide conjugates—which, for example, ensures adequate coverage of a target polynucleotide in a shotgun sequencing operation, and selecting a small sample which ensures that a minimal number of doubles will be present. In most embodiments, the presence of doubles merely adds an additional source of noise or, in the case of sequencing, a minor complication in scanning and signal processing, as regions of tag complements simultaneously giving multiple signals can simply be ignored. As used herein, the term "substantially all" in reference to attaching tags to polynucleotides is meant to reflect the statistical nature of the sampling procedure employed to obtain a population of tag-molecule conjugates essentially free of doubles. The meaning of substantially all in terms of actual percentages of tag-molecule conjugates depends on how the tags are being employed. Preferably, for nucleic acid sequencing and idenwhere the "T" or tag primer binding site and the "S" or sequencing primer binding site are used with the appropriate primers to amplify the insert of the cloning vector to form PCR amplicons for subsequent analysis. The cleavage sites are used to excise the tag from the amplicons, after steps of PCR amplification and identification of a terminal nucleotide. As noted below, after amplifications, it is important that the target polynucleotides be protected from undesired cleavage by the nucleases employed in the identification and shortening cycles. Preferably, this is accomplished by methylation and careful selection of restriction endonucleases.

Sequencing Tagged Polynucleotides

Figure 2:
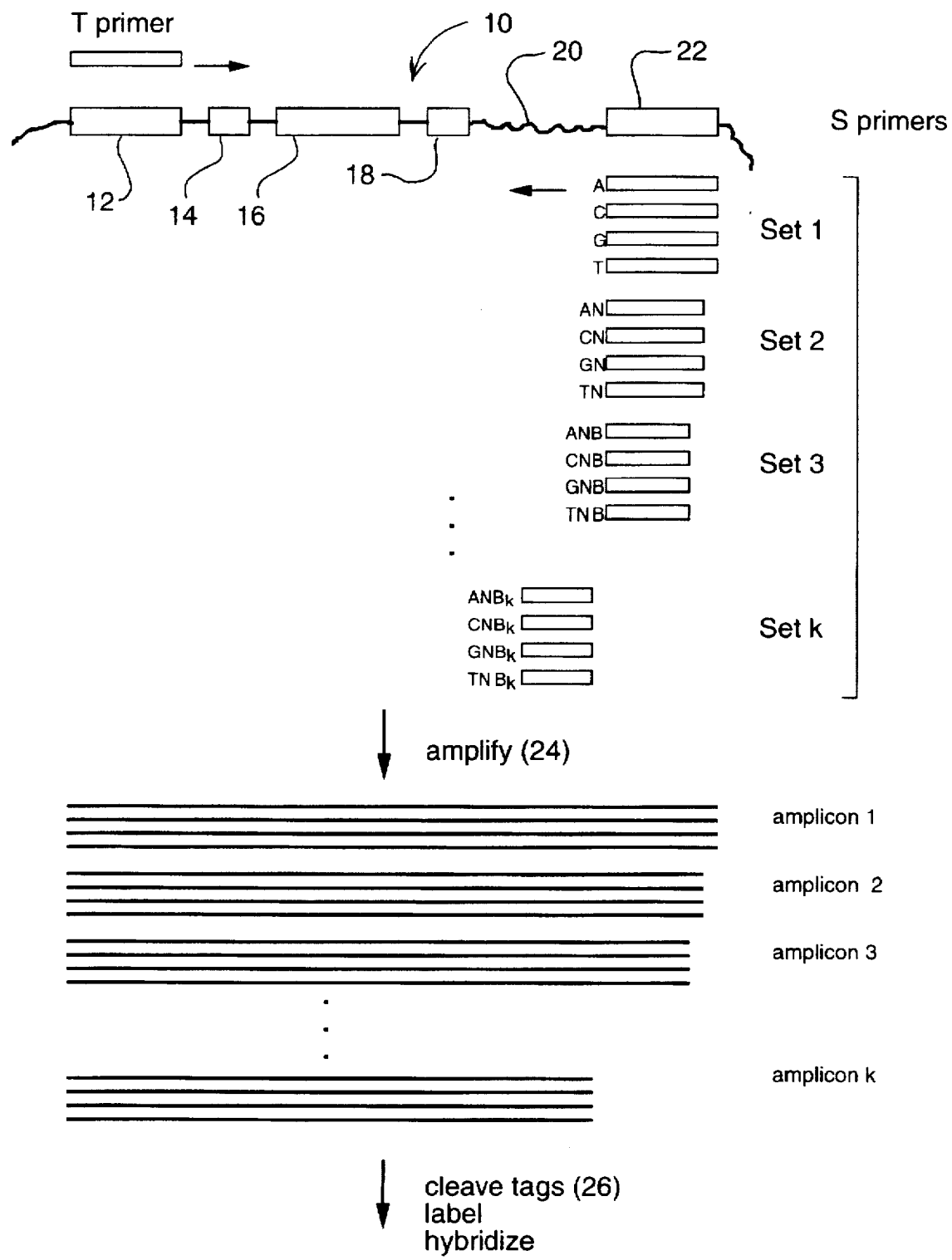
FIG. 2 illustrates the use of S and T primers in one embodiment of the invention.

In a preferred embodiment of the invention, the identification of the terminal nucleotides of polynucleotide inserts is accomplished by selectively amplifying sequences that form perfectly matched duplexes with the 3' end of the S primers. As illustrated in FIG. 2, in each identification cycle multiple sets of S primers are used with the same T primer to produce PCR amplicons. Segments of cloning vector 10 containing T primer binding site 12, cleavage site 14, tag 16, cleavage site 18, polynucleotide 20, and S primer binding site 22 are amplified in separate PCRs for each of the different S primers, which in FIG. 2 number 4k. The S primers of sets 1 through k form duplexes with the S primer binding site and 1 to k terminal nucleotides of the polynucleotide, respectively. In FIG. 2, "N" represents a mixture of the four natural nucleotides, A, C, G, and T. Thus, the S primers of set 2 are each mixtures of 4 primers: one having a 3' terminal A and a penultimate nucleotide of A, C, G, or T; one having a 3' terminal C and a penultimate nucleotide of A, C, G, or T; one having a 3' terminal G and a penultimate nucleotide of A, C, G, or T; and one having a 3' terminal T and a penultimate nucleotide of A, C, G, or T. In sets 3 through k, "B" represents a degeneracy-reducing analog, or a mixture of such analogs and natural nucleotides. For example, B could consist of C and deoxyinosine.

Such analogs are well known and are describe in Kong Thoo Lin et al, Nucleic Acids Research, 20: 5149–5152;

U.S. Pat. No. 5,002,867; Loakes et al. Nucleic Acids Research, 22: 4039–4043 (1994); Nichols et al, Nature, 369: 492–493 (1994); and like references.

The penultimate N's in S primers 2 through k could also be degeneracy reducing analogs, provided that the presence of such an analog had no effect on the base pairing or extension of the terminal nucleotide. Indeed, it is not crucial that an S primer form a perfectly matched duplex with its binding site and target polynucleotide over the primer's entire length. It is only required that the terminal nucleotide base pair correctly. Preferably, the S and T primers have approximately equal melting and annealing temperatures, and are in the range of 12 to 30 nucleotides in length.

After carrying out the PCRS, k sets of 4 amplicons are produced. The 4k amplicons carry the following information: In set 1, amplicons made with S primers having a terminal A indicate polynucleotides whose first nucleotide is T; amlicons made with S primers having a terminal C indicate polynucleotides whose first nucleotide is G; and so on. In set 2, amplicons made with S primers having a terminal AN indicate polynucleotides whose second nucleotide is T; amplicons made with S primers having a terminal CN indicate polynucleotides whose second nucleotide is G; and so on. Likewise, for amplicons of sets 3 through k, the identities of the nucleotides of the 3rd through kth positions are indicated, respectively. To extract this information, the tags in the amplicons must be excised, labeled, rendered single stranded, and hybridized to their tag complements on a spatially addressable array. Tags 16 are excised by cleaving with restriction endonucleases directed to sites 14 and 18. Preferably, the T primer is constructed to have a means for isolating the amplicons, such as a biotin moiety or a double stranded segment which can form a triplex structure with an anchored single stranded oligonucleotide. Preferably, after separation, the tags of each of the four amplicons of each set are separately labelled, e.g. with a spectrally resolvable fluorescent dye. Thus, all the tags in amplicon made from S primers terminating in A have the same label which can be distinguished from the labels for C, G, and T. The same holds for tags in amplicons made from S primers terminating in C, G, and T, regardless of the set number. Thus, when the tags of the nth set are simultaneously applied to the spatially addressable sites, the identity of the nucleotides at the nth position of all the target polynucleotides are determined.

Tags can be labeled in a variety of ways, including the direct or indirect attachment of radioactive moieties, fluorescent moieties, colorimetric moieties, chemiluminescent markers, and the like. Many comprehensive reviews of methodologies for labeling DNA and constructing DNA probes provide guidance applicable to labelling tags of the present invention. Such reviews include Kricka, editor, Nonisotopic DNA Probe Techniques (Academic Press, San Diego, 1992); Haugland, Handbook of Fluorescent Probes and Research Chemicals (Molecular Probes, Inc., Eugene, 1992); Keller and Manak, DNA Probes, 2nd Edition (Stockton Press, New York, 1993); and Eckstein, editor, Oligonucleotides and Analogues: A Practical Approach (IRL Press, Oxford, 1991); Kessler, editor, Nonradioactive Labeling and Detection of Biomolecules (Springer-Verlag, Berlin, 1992); and the like.

Preferably, the tags are labeled with one or more fluorescent dyes, e.g. as disclosed by Menchen et al. U.S. Pat. No. 5,188,934; and Begot et al International application PCT/US90/05565.

Preferably, the S primers are constructed to have a double stranded segment capable of binding to an anchored single stranded oligonucleotide for separation, e.g. as taught by Ji et al, Anal. Chem. 65: 1323–1328 (1993). Thus, for example, magnetic beads carrying such a single stranded oligonucleotide can be used to capture the amplicons and transfer them to a separate vessel containing a nuclease to cleave the tag, e.g. at cleavage site 18. Preferably, the T primer contains a 5' biotin which permits the release tag to be captured and conveniently labeled. After capture, e.g. via avidinated magnetic beads, the 3' strands of the double stranded segment are stripped back to the tag by the use of T4 DNA polymerase, or like enzyme, in the presence of a deoxynucleoside triphosphate (dNTP) corresponding to the nucleotide flanking the tag. Thus, provided that the flanking nucleotides are not present elsewhere along the strand to the 3' ends, the 3'→5' exonuclease activity of the polymerase will strip back the 3' strand to the flanking nucleotides, at which point an exchange reaction will be initiated that prevents further stripping past the flanking nucleotides. The 3' ends of the tag can then be labeled in an extension reaction with labeled dNTPs. After labelling the non-biotinylated strand can be removed by denaturation and applied to the spatially addressable array for detection.

After the labeled tags are hybridized to their tag complements and detected, the tags are removed by washing so that labeled tags from the next set of amplicons can be applied. As long as the amplicon number from which the tags arose are kept track of, the ordering of hybridizations is not crucial. Preferably, hybridizations are done in the same order as the order of the corresponding nucleotide in the target sequence.

The extent to which the S primers can overlap the target polynucleotide for identifying successive nucleotides is limited by the degeneracy, or complexity, of the primer mixture as the overlap increases. This difficulty is addressed by periodically cleaving off the identified nucleotides from the target polynucleotide, and then starting the identification cycle over again on the shortened target polynucleotide. Such cleavage is effected by providing an S primer binding region with a recognition site of a nuclease that has a cleavage site separate from its recognition site, so that the nuclease will be positioned by the recognition site to cleave the target polynucleotide a predetermined number of nucleotides from the border of the S primer binding site. Such a nuclease is referred to herein as a "stepping" nuclease. Preferably, a type IIs restriction endonuclease is employed for as a stepping nuclease in the invention. Prior to cleavage the target polynucleotide must be treated, e.g. by methylation, to prevent fortuitous cleavage because of internal recognition sites of the stepping nuclease being employed. After cleavage, the strand bearing the S primer binding site is removed, e.g. via triplex capture on magnetic beads, and an adaptor containing a replacement S primer binding site is ligated to the remaining strand. The adaptor contains a degenerate protruding strand that is compatible with the cleavage produced by the stepping nuclease. For example, if the type IIs nuclease Bbv I is employed, the adaptor may have the following structure:

where N is defined as above and the underlining indicates the location of a Bbv I recognition site.

A stepping nuclease employed in the invention need not be a single protein, or consist solely of a combination of proteins. A key feature of the stepping nuclease, or of the combination of reagents employed as a stepping nuclease, is that its (their) cleavage site be separate from its (their) recognition site. The distance between the recognition site of a stepping nuclease and its cleavage site will be referred to herein as its "reach." By convention, "reach" is defined by two integers which give the number of nucleotides between the recognition site and the hydrolyzed phosphodiester bonds of each strand. For example, the recognition and cleavage properties of Fok I is typically represented as "GGATG(9/13)" because it recognizes and cuts a double stranded DNA as follows:

5'- ... NNGGATGNNNN NNNNNNNNN ...

3'- ... NNCCTACNNNNNNNNNNNNN NNNNNN ...

where the bolded nucleotides are Fok I's recognition site and the N's are arbitrary nucleotides and their complements.

Preferably, stepping nucleases employed in the invention are natural protein endonucleases (i) whose recognition site is separate from its cleavage site and (ii) whose cleavage results in a protruding strand on the target polynucleotide. Most preferably, type IIs restriction endonucleases are employed as stepping nucleases in the invention, e.g. as described in Szybalski et al, Gene, 100: 13–26 (1991); Roberts et al, Nucleic Acids Research, 21: 3125–3137 (1993); and Livak and Brenner, U.S. Pat. No. 5,093,245. Exemplary type IIs nucleases include Alw XI, Bsm AI, Bbv I, Bsm FI, Sts I, Hga I, Bsc AI, Bbv II, Bce fI, Bce 85I, Bcc I, Bcg I, Bsa I, Bsg I, Bsp MI, Bst 71 I, Ear I, Eco 57I, Esp 3I, Fau I, Fok I, Gsu I, Hph I, Mbo II, Mme I, Rle AI, Sap I, Sfa NI, Taq II, Tth 111II, Bco 5I, Bpu AI, Fin I, Bsr DI, and isoschizomers thereof. Preferred nucleases include Fok I, Bbv I, Hga I, Ear I, and Sfa NI.

Preferably, prior to nuclease cleavage steps, usually at the start of an identification cycle, the target polynucleotide is treated to block the recognition sites and/or cleavage sites of the nuclease being employed. This prevents undesired cleavage of the target polynucleotide because of the fortuitous occurrence of nuclease recognition sites at interior locations in the target polynucleotide. Blocking can be achieved in a variety of ways, including methylation and treatment by sequence-specific aptamers, DNA binding proteins, or oligonucleotides that form triplexes. Whenever natural protein endonucleases are employed, recognition sites can be conveniently blocked by methylating the target polynucleotide with the cognate methylase of the nuclease being used. That is, for most if not all type II bacterial restriction endonucleases, there exists a so-called "cognate" methylases that methylates its recognition site. Many such methylases are disclosed in Roberts et al (cited above) and Nelson et al, Nucleic Acids Research, 21: 3139–3154 (1993), and are commercially available from a variety of sources, particularly New England Biolabs (Beverly, Mass.).

Apparatus for Observing Detection Signals at Spatially Addressable Sites

Preferably, a spatially addressable array is established by fixing microparticle containing tag complements to a solid phase surface.

Preferably, whenever light-generating signals, e.g. chemiluminescent, fluorescent, or the like, are employed to detect tags, microparticles are spread on a planar substrate, e.g. a glass slide, for examination with a scanning system, such as described in International patent applications PCT/US91/09217, PCT/NL90/00081, and PCT/US95/01886. The scanning system should be able to reproducibly scan the substrate and to define the positions of each microparticle in a predetermined region by way of a coordinate system. In polynucleotide sequencing applications, it is important that the positional identification of microparticles be repeatable in successive scan steps.

Figure 3:
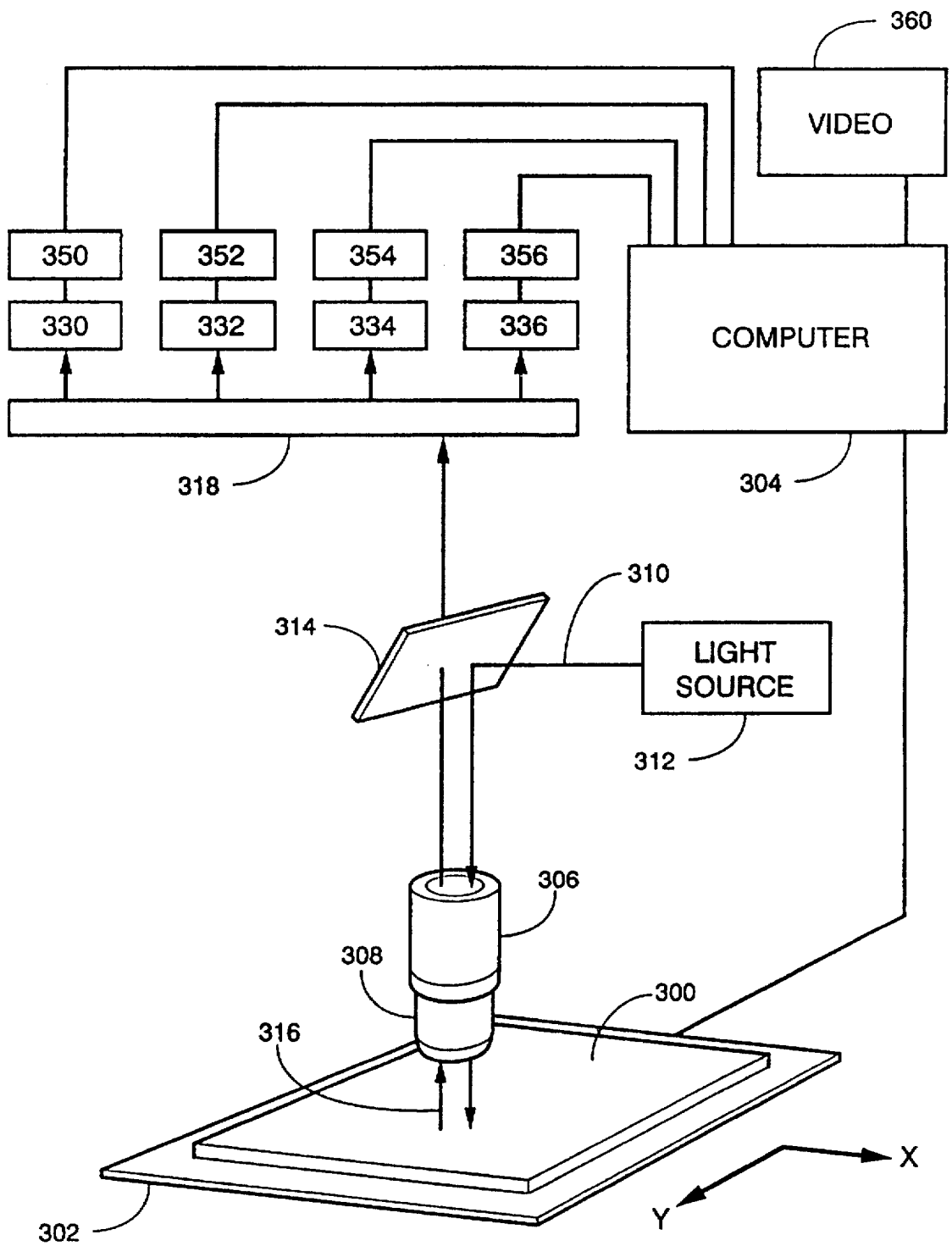
FIG. 3 diagrammatically illustrates an apparatus for detecting labeled tags on a spatially addressable array of tag complements.

Such scanning systems may be constructed from commercially available components, e.g. x-y translation table controlled by a digital computer used with a detection system comprising one or more photomultiplier tubes, or alternatively, a CCD array, and appropriate optics, e.g. for exciting, collecting, and sorting fluorescent signals. In some embodiments a confocal optical system may be desirable. An exemplary scanning system suitable for use in four-color sequencing is illustrated diagrammatically in FIG. 3. Substrate 300, e.g. a microscope slide with fixed microparticles, is placed on x-y translation table 302, which is connected to and controlled by an appropriately programmed digital computer 304 which may be any of a variety of commercially available personal computers, e.g. 486-based machines or PowerPC model 7100 or 8100 available form Apple Computer (Cupertino, Calif.). Computer software for table translation and data collection functions can be provided by commercially available laboratory software, such as Lab Windows, available from National Instruments.

Substrate 300 and table 302 are operationally associated with microscope 306 having one or more objective lenses 308 which are capable of collecting and delivering light to microparticles fixed to substrate 300. Excitation beam 310 from light source 312, which is preferably a laser, is directed to beam splitter 314, e.g. a dichroic mirror, which re-directs the beam through microscope 306 and objective lens 308 which, in turn, focuses the beam onto substrate 300. Lens 308 collects fluorescence 316 emitted from the microparticles and directs it through beam splitter 314 to signal distribution optics 318 which, in turn, directs fluorescence to one or more suitable opto-electronic devices for converting some fluorescence characteristic, e.g. intensity, lifetime, or the like, to an electrical signal. Signal distribution optics 318 may comprise a variety of components standard in the art, such as bandpass filters, fiber optics, rotating mirrors, fixed position mirrors and lenses, diffraction gratings, and the like. As illustrated in FIG. 5, signal distribution optics 318 directs fluorescence 316 to four separate photomultiplier tubes, 330, 332, 334, and 336, whose output is then directed to pre-amps and photon counters 350, 352, 354, and 356. The output of the photon counters is collected by computer 304, where it can be stored, analyzed, and viewed on video 360. Alternatively, signal distribution optics 318 could be a diffraction grating which directs fluorescent signal 318 onto a CCD array.

The stability and reproducibility of the positional localization in scanning will determine, to a large extent, the resolution for separating closely spaced microparticles. Preferably, the scanning systems should be capable of resolving closely spaced microparticles, e.g. separated by a particle diameter or less. Thus, for most applications, e.g.

using CPG microparticles, the scanning system should at least have the capability of resolving objects on the order of 5–100 nm. Even higher resolution may be desirable in some embodiments, but with increase resolution, the time required to fully scan a substrate will increase; thus, in some embodiments a compromise may have to be made between speed and resolution. Increases in scanning time can be achieved by a system which only scans positions where microparticles are known to be located, e.g. from an initial full scan. Preferably, microparticle size and scanning system resolution are selected to permit resolution of fluorescently labeled microparticles randomly disposed on a plane at a density between about ten thousand to one hundred thousand microparticles per cm$^2$.

In sequencing applications, microparticles can be fixed to the surface of a substrate in variety of ways. The fixation should be strong enough to allow the microparticles to undergo successive cycles of reagent exposure and washing without significant loss. When the substrate is glass, its surface may be derivatized with an alkylamino linker using commercially available reagents, e.g. Pierce Chemical, which in turn may be cross-linked to avidin, again using conventional chemistries, to form an avidinated surface. Biotin moieties can be introduced to the microparticles in a number of ways.

In an alternative, when DNA-loaded microparticles are applied to a glass substrate, the DNA nonspecifically adsorb to the glass surface upon several hours, e.g. 24 hours, incubation to create a bond sufficiently strong to permit repeated exposures to reagents and washes without significant loss of microparticles. Such a glass substrate may be a flow cell, which may comprise a channel etched in a glass slide. Preferably, such a channel is closed so that fluids may be pumped through it and has a depth sufficiently close to the diameter of the microparticles so that a monolayer of microparticles is trapped within a defined observation region.

Kits for Implementing the Method of the Invention

The invention includes kits for carrying out the various embodiments of the invention. Preferably, kits of the invention include a repertoire of tag complements attached to a solid phase support. Additionally, kits of the invention may include the corresponding repertoire of tags, e.g. as primers for amplifying the polynucleotides to be sorted or as elements of cloning vectors. Preferably, the repertoire of tag complements are attached to microparticles. Kits may also contain appropriate buffers for enzymatic processing, detection chemistries, e.g. fluorescent or chemiluminescent components for labelling tags, and the like, instructions for use, processing enzymes, such as ligases, polymerases, transferases, and so on. In an important embodiment for sequencing, kits may also include substrates, such as a avidinated microscope slides or microtiter plates, for fixing microparticles for processing.

EXAMPLE 1

Construction of a Tag Library

An exemplary tag library is constructed as follows form the chemically synthesized 9-word tags of nucleotides A, G, and T defined by the formula:

3'-TGGC-[$^4$(A,G,T)$_9$]-CCCCp where "[$^4$((A,G,T)$_9$]" indicates a tag mixture where each tag consists of nine 4-mer words of A, G, and T; and "p" indicate a 5' phosphate. This mixture is ligated to the following right and left primer binding regions:

5'-AGTGGCTGGGCATCGGACCG
TCACCGACCCGTAGCCp

LEFT

5'-GGGGCCCAGTCAGCGTCGAT
GGGTCAGTCGCAGCTA

RIGHT

The right and left primer binding regions are ligated to the above tag mixture, after which the single stranded portion of the ligated structure is filled with DNA polymerase then mixed with the right and left primers indicated below and amplified to give a tag library.

Left primer:
5'-AGTGGCTGGGCATCGGACCG

5'-AGTGGCTGGGCATCGGACCG-[$^4$((A, G, T)$_9$]-GGGGCCCAGTCAGCGTCGAT
TCACCGACCCGT<u>AGCCTGGC</u>-[$^4$((A, G, T)$_9$]-CCCCGGGTCAGT<u>CGCAGCT</u>A

CCCCGGGTCAGTCGCAGCTA-5'

Right primer

The underlined portion of the left primer binding region indicates a Rsr II recognition site. The left-most underlined region of the right primer binding region indicates recognition sites for Bsp 120I, Apa I, and Eco O 109I, and a cleavage site for Hga I. The right-most underlined region of the right primer binding region indicates the recognition site for Hga I. Optionally the right or left primers may be synthesized with a biotin attached (using conventional reagents, e.g. available from Clontech Laboratories, Palo Alto, Calif.) to facilitate purification after amplification and/or cleavage.

EXAMPLE 2

Construction of a Plasmid Library of Tag-Polynucleotide Conjugates for cDNA "Signature" Sequencing cDNA is produced from an mRNA sample by conventional protocols using pGGCCCT$_{15}$(A or G or C) as a primer for first strand synthesis anchored at the boundary of the poly A region of the mRNAs and N$_8$(A or T)GATC as the primer for second strand synthesis. That is, both are degenerate primers such that the second strand primer is present in two forms and the first strand primer is present in three forms. The GATC sequence in the second strand primer corresponds to the recognition site of Mbo I; other four base recognition sites could be used as well, such as those for Bam H1, Sph I, Eco RI, or the like. The presence of the A and T adjacent to the restriction site of the second strand primer ensures that a stripping and exchange reaction can be used in the next step to generate a five-base 5' overhang of "GGCCC". The first strand primer is annealed to the mRNA sample and extended with reverse transcriptase, after which the RNA strand is degraded by the RNase H activity of the reverse transcriptase leaving a single stranded cDNA. The second strand primer is annealed and extended with a DNA polymerase using conventional protocols. After second strand synthesis, the resulting cDNAs are methylated with CpG methylase (New England Biolabs, Beverly, Mass.) using manufacturer's protocols. The 3' strands of the cDNAs are then cut back with the above-mentioned stripping and exchange reaction using T4 DNA polymerase in the presence of dATP and dTTP, after which the cDNAs are ligated to the tag library of Example 1 previously cleaved with Hga I to give the following construct:

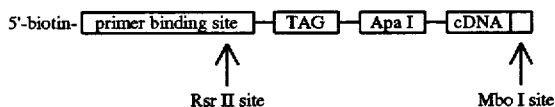

Separately, the following cloning vector is constructed, e.g. starting from a commercially available plasmid, such as a Bluescript phagemid (Stratagene, La Jolla, Calif.).

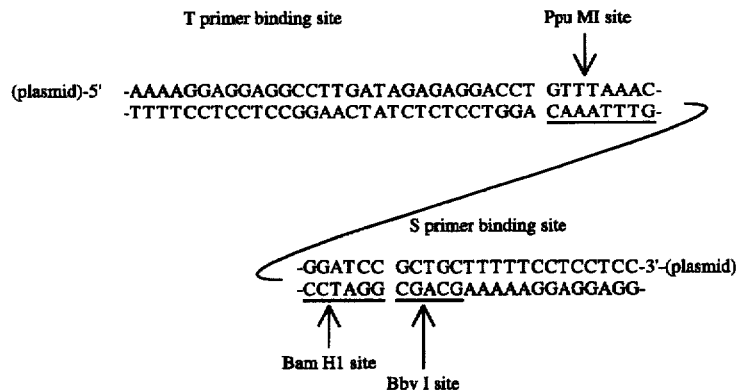

The plasmid is cleaved with Ppu MI and Pme I and then methylated with DAM methylase. The tag-containing construct is cleaved with Rsr II and then ligated to the open plasmid, after which the conjugate is cleaved with Mbo I and Bam HI to permit ligation and closing of the plasmid. The plasmid is then amplified and isolated for use as a template in the selective amplifications using the S and T primers.

EXAMPLE 3

Signature Sequencing of a cDNA Library

The plasmid constructed in Example 2 is used as a base library for generating amplicons with S and T primers. The following T primer is employed:

biotin-5'-IIIIIIIAAAAGGAGGAGGCCTTGA where the I's are deoxyinosines added to balance the anneal and melting temperatures of the S and T primers. The following 32 S primers are employed:

XCGACGAAAAAGGAGGAGGIIIIII-5'
XNCGACGAAAAAGGAGGAGGIIIII
XNBCGACGAAAAAGGAGGAGGIIII
XNBBCGACGAAAAAGGAGGAGGIIII
XNBBBCGACGAAAAAGGAGGAGGIII
XNBBBBCGACGAAAAAGGAGGAGGII
XNBBBBBCGACGAAAAAGGAGGAGGI
XNBBBBBBCGACGAAAAAGGAGGAGG
            ↑
         Bbv I site where X represents one of the four nucleotides, A, C, G, and T so that each of the above sequences represents four different mixtures of S primers, and where N represents a mixture of the four natural nucleotides and B represents a mixture of I and C, which serve as dengeneracy-reducing analogs. Clearly, other spacer nucleotide may also be used.

The plasmid DNA is methylated with Hae III methylase and dispersed into 32 separate vessels, e.g. wells of a microtiter plate, where PCRs using the above primers are performed. Preferably, the reactions are arranged in 8 rows of 4 reactions: one row for each nucleotide position being interrogated and one column for each 3' terminal nucleotide of the S primer. 8 rows are required because the reach of Bbv I is (8/12), so that after 8 nucleotides are identified by the above PCRs, the nucleotides are remove from the cDNA by Bbv I cleavage.

After PCR amplification, the amplicons from each reaction are separately captured on magnetic beads carrying a single stranded sequence that forms a triplex with the S primers. The beads are then transferred to reaction mixtures containing Apa I, which cleaves all strand not containing methyl groups, i.e. all the strands that have been selectively amplified. The released strands are next captured via their biotinylated T primers with magnetic beads coated with avidin and transferred to reaction vessels where their 3' ends are stripped in the presence of T4 DNA polymerase and dGTP, as shown below:

After cleavage with Apa I

Here dUTP* represents a labeled dUTP and ddATP represents dideoxyadenosine triphosphate. Preferably, dUTP is labeled with a separate spectrally resolvable fluorescent dye for each of the four column PCRs. The released tags for each of the eight row PCRs are mixed and are applied to the spatially addressable array for hybridization to their complements and detection.

After, or concurrently with, the 32 PCRs, Bbv I is used to shorten the cDNA inserts of the library. An amplicon is produced from a fresh sample of plasmid using the following S and T primers:

T primer: 5'-AAAAGGAGGAGGCCTTGA

S primer: 3'-CGACGAAAAGGAGGAGG-biotin

After amplification, the amplicon is methylated to protect internal Bbv I sites, its 3' ends are stripped using T4 DNA polymerase and dGTP, after which the recessed strands are filled in by the addition of dTTP and dCTP. The amplicon is then cleaved with Bbv I and the S primer segment is removed with magnetic beads coated with avidin. The following adaptor mixture containing a new S primer binding site is then ligated to the T primer segment:

5'-GGAGGAGGAAAAAGCAGC CCTCCTCCTTTT
TCGTCGNNNN

The ligated fragment is then amplified for the next cycle of selective amplifications withe the 32 S primers described above.

APPENDIX I

Exemplary computer program for generating minimally cross hybridizing sets

```
Program minxh
c
c
c
      integer*2 subl(6),mset1(1000,6),mset2(1000,6)
      dimension nbase (6)
```

-continued

```
c
c
      write(*,*)'ENTER SUBUNIT LENGTH'
      read(*, 100)nsub
      format(i1)
      open(1, file='sub4.dat', form='formatted', status='new')
c
c
      nset=0
      do 7000 m1=1,3
        do 7000 m2=1,3
          do 7000 m3=1,3
            do 7000 m4=1,3
              sub1(1)=m1
              sub1(2)=m2
              sub1(3)=m3
              sub1(4)=m4
c
c
      ndiff=3
c
c
c
c                Generate set of subunits differing from
c                sub1 by at least ndiff nucleotides.
c                Save in mset1.
c
      jj=1
      do 900 j=1,nsub
        mset1(1,j)=sub1(j)
c
c
      do 1000 k1=1,3
        do 1000 k2=1,3
          do 1000 k3=1,3
            do 1000 k4=1,3
c
c
              nbase(1)=k1
              nbase(2)=k2
              nbase (3)=k3
              nbase(4)=k4
c
      n=0
      do 1200 j=1,nsub
        if(sub1(j) .eq.1 .and. nbase(j) .ne.1 .or.
     1     sub1(j) .eq.2 .and. nbase(j) .ne.2 .or.
     3     sub1(j) .eq.3 .and. nbase(j) .ne.3) then
          n=n+1
        endif
1200  continue
c
c
      if(n.ge.ndiff) then
c
c
c                             If number of mismatches
c                             is greater than or equal
c                             to ndiff then record
c                             subunit in matrix mset
c
      jj=jj+1
      do 1100 i=1,nsub
        mset1(jj,i)=nbase(i)
      endif
c
c
1000  continue
c
c
      do 1325 j2=1,nsub
        mset2(1,j2)=mset1(1,j2)
        mset2(2,j2)=mset1(2,j2)
```

Compare subunit 2 from
                           mset1 with each successive
                           subunit in mset1, i.e. 3,
                           4,5, . . . etc. Save those

```
c                                with mismatches .ge. ndiff
c                                in matrix mset2 starting at
c                                position 2.
c                                  Next transfer contents
c                                of mset2 into mset1 and
c                                start
c                                comparisons again this time
c                                starting with subunit 3.
c                                Continue until all subunits
c                                undergo the comparisons.
c
c
          npass=0
c
c
1700      continue
          kk=npass+2
          npass=npass+1
c
          do 1500 m=npass+2,jj
            n=0
            do 1600 j=1,nsub
              if(mset1(npass+1,j) .eq.1.and.mset1(m,j) .ne.1.or.
     2           mset1(npass+1,j) .eq.2.and.mset1(m,j) .ne.2.or.
                 mset1(npass+1,j) .eq.3.and.mset1(m,j) .ne.3) then
                n=n+1
              endif
1600        continue
            if(n.ge.ndiff) then
              kk=kk+1
              do 1625 i=1,nsub
1625            mset2(kk,i)=mset1(m,i)
            endif
1500      continue
c
c                                kk is the number of
c                                subunits stored in mset2
c
c
c                                Transfer contents of mset2
c                                into mset1 for next pass.
c
c
          do 2000 k=1,kk
            do 2000 m=1,nsub
2000          mset1(k,m)=mset2(k,m)
          if(kk.lt.jj) then
            jj=kk
            goto 1700
          endif
c
c
          nset=nset+1
          write (1,7009)
7009      format(/)
          do 7008 k=1,kk
7008        write(1,7010) (mset1(k,m) ,m=1,nsub)
7010      format(4i1)
          write(*,*)
          write(*,120) kk,nset
120       format(1x, 'Subunits in set=',i5,2x, 'Set No=',i5)
7000      continue
          close(1)
c
c
          end
```

---

---

I claim:

1. A method for simultaneously determining the nucleotide sequences of a population of polynucleotides, the method comprising the steps of:

(a) attaching an oligonucleotide tag from a repertoire of tags to each polynucleotide of the population to form tag-polynucleotide conjugates such that substantially all different polynucleotides have different oligonucleotide tags attached;

(b) selectively amplifying tag-polynucleotide conjugates with primers whose 3' ends form perfectly matched duplexes with one or more terminal nucleotides of the polynucleotides of the population;

(c) labeling each tag of the selectively amplified tag-polynucleotide conjugates according to the identity of the one or more terminal nucleotides of its associated polynucleotide;

(d) cleaving the tags from the selectively amplified tag-polynucleotide conjugates; and (e) sorting the labeled tags onto a spatially addressable array of tag complements for detection of the labeled tags and identification of the one or more nucleotides of each polynucleotide.

2. The method of claim 1 further including the steps of (f) cleaving said identified nucleotides from said polynucleotides; and (g) repeating said steps (b) through (f).

3. The method of claim 2 wherein said step of selectively amplifying includes amplifying said tag-polynucleotide conjugates by a polymerase chain reaction using said primers and a second primer.

4. A method for simultaneously determining the nucleotide sequences of a population of polynucleotides, the method comprising the steps of:

(a) attaching an oligonucleotide tag from a repertoire of tags to each polynucleotide of the population to form tag-polynucleotide conjugates such that substantially all different polynucleotides have different oligonucleotide tags attached;

(b) amplifying the tag-polynucleotide conjugates by a polymerase chain reaction using a first primer and a second primer, the second primer having a 3' terminal nucleotide and forming a duplex with a primer binding site and one or more nucleotides at one end of the tag-polynucleotide conjugate, such that a tag-polynucleotide conjugate is amplified only if the defined 3' terminal nucleotide basepairs with a nucleotide of the tag-polynucleotide conjugate;

(c) cleaving the tags from the tag-polynucleotide conjugates;

(d) labeling the tags according to the identity of the defined 3' terminal nucleotide of the second primer; and (e) sorting the labeled tags onto a spatially addressable array of tag complements for detection of the labeled tags and identification of the one or more nucleotides of each polynucleotide.

5. The method of claim 4 further including the steps of (f) cleaving said identified nucleotides from said polynucleotides; and (g) repeating said steps (b) through (f).

6. The method of claim 3 wherein said oligonucleotide tags comprise a plurality of subunits wherein each subunit consists of an oligonucleotide having a length of from three to six nucleotides or from three to six basepairs, the subunits being selected from a minimally cross-hybridizing set, wherein a duplex between a subunit of such a set and a complement of any other subunit of the set would have at least two mismatches.

7. The method of claim 6 wherein said oligonucleotide tags and said tag complements are single stranded.

8. The method of claim 5 wherein said oligonucleotide tags comprise a plurality of subunits wherein each subunit consists of an oligonucleotide having a length of from three to six nucleotides or from three to six basepairs, the subunits being selected from a minimally cross-hybridizing set, wherein a duplex between a subunit of such a set and a complement of any other subunit of the set would have at least two mismatches.

9. The method of claim 8 wherein said oligonucleotide tags and said tag complements are single stranded.

10. A method for simultaneously determining the nucleotide sequences of a population of polynucleotides, the method comprising the steps of:

(a) attaching an oligonucleotide tag from a repertoire of tags to each polynucleotide of the population;

(b) sampling the population of polynucleotides such that substantially all different polynucleotides in the population have different oligonucleotide tags attached;

(c) amplifying the sampled polynucleotides by a polymerase chain reaction using a first primer and a second primer, the second primer having a 3' terminal nucleotide and forming a duplex with a primer binding site and one or more nucleotides at one end of the polynucleotide, such that a polynucleotide is amplified only if the defined 3' terminal nucleotide basepairs with a nucleotide of the polynucleotide;

(d) copying the tags from the polynucleotides;

(e) labeling the copied tags according to the identity of the defined 3' terminal nucleotide of the second primer; and (f) sorting the labeled tags onto a spatially addressable array of tag complements for detection of the labeled tags and identification of the one or more nucleotides of each polynucleotide.

11. The method of claim 10 further including the steps of (g) cleaving said identified nucleotides from said polynucleotides; and (h) repeating said steps (c) through (g).

12. The method of claim 11 wherein said oligonucleotide tags comprise a plurality of subunits wherein each subunit consists of an oligonucleotide having a length of from three to six nucleotides or from three to six basepairs, the subunits being selected from a minimally cross-hybridizing set, wherein a duplex between a subunit of such a set and a complement of any other subunit of the set would have at least two mismatches.

13. The method of claim 12 wherein said oligonucleotide tags and said tag complements are single stranded.

* * * * *

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 19 nucleotides
        ( B ) TYPE: nucleic acid
        ( C ) STRANDEDNESS: double
        ( D ) TOPOLOGY: linear ( x i ) SEQUENCE DESCRIPTION: SEQ ID NO: 1:

AAAGAAAGGA AGGGCAGCT                          19

( 2 ) INFORMATION FOR SEQ ID NO: 2:

( i ) SEQUENCE CHARACTERISTICS:
        ( A ) LENGTH: 20 nucleotides
        ( B ) TYPE: nucleic acid
        ( C ) STRANDEDNESS: double
        ( D ) TOPOLOGY: linear ( x i ) SEQUENCE DESCRIPTION: SEQ ID NO: 2:

NNCCTACNNN NNNNNNNNNN                        20

( 2 ) INFORMATION FOR SEQ ID NO: 3:

( i ) SEQUENCE CHARACTERISTICS:
        ( A ) LENGTH: 20 nucleotides
        ( B ) TYPE: nucleic acid
        ( C ) STRANDEDNESS: double
        ( D ) TOPOLOGY: linear ( x i ) SEQUENCE DESCRIPTION: SEQ ID NO: 3:

AGTGGCTGGG CATCGGACCG    20

( 2 ) INFORMATION FOR SEQ ID NO: 4:

( i ) SEQUENCE CHARACTERISTICS:
        ( A ) LENGTH: 20 nucleotides
        ( B ) TYPE: nucleic acid
        ( C ) STRANDEDNESS: double
        ( D ) TOPOLOGY: linear ( x i ) SEQUENCE DESCRIPTION: SEQ ID NO: 4:

GGGGCCCAGT CAGCGTCGAT    20

( 2 ) INFORMATION FOR SEQ ID NO: 5:

( i ) SEQUENCE CHARACTERISTICS:
        ( A ) LENGTH: 62 nucleotides
        ( B ) TYPE: nucleic acid
        ( C ) STRANDEDNESS: double
        ( D ) TOPOLOGY: linear ( x i ) SEQUENCE DESCRIPTION: SEQ ID NO: 5:

AAAAGGAGGA GGCCTTGATA GAGAGGACCT GTTTAAACGG ATCCGCTGCT    50

TTTTCCTCCT CC    62

( 2 ) INFORMATION FOR SEQ ID NO: 6:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 6:

NNNNNNNNAA AAGGAGGAGG CCTTGA    26

( 2 ) INFORMATION FOR SEQ ID NO: 7:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 7:

NCGACGAAAA AGGAGGAGGN NNNNN    26

( 2 ) INFORMATION FOR SEQ ID NO: 8:

( i ) SEQUENCE CHARACTERISTICS:
        ( A ) LENGTH: 43 nucleotides
        ( B ) TYPE: nucleic acid
        ( C ) STRANDEDNESS: double
        ( D ) TOPOLOGY: linear ( x i ) SEQUENCE DESCRIPTION: SEQ ID NO: 8:

NNNNNNNNAG AGAGAGAGAG GAGAGAGAGA GTAGAGAGGA CCG    43

(2) INFORMATION FOR SEQ ID NO: 9:

(i) SEQUENCE CHARACTERISTICS:
        (A) LENGTH: 12 nucleotides
        (B) TYPE: nucleic acid
        (C) STRANDEDNESS: single
        (D) TOPOLOGY: linear (xi) SEQUENCE DESCRIPTION: SEQ ID NO: 9:

AUCUCUCCUG GC            12